United States Patent [19]

Walter

[11] Patent Number: 4,841,150

[45] Date of Patent: Jun. 20, 1989

[54] REFLECTION TECHNIQUE FOR THERMAL MAPPING OF SEMICONDUCTORS

[75] Inventor: Martin J. Walter, Lee, N.Y.

[73] Assignee: The United States of America as represented by the Secretary of the Air Force, Washington, D.C.

[21] Appl. No.: 138,238

[22] Filed: Dec. 28, 1987

[51] Int. Cl.[4] ..................... G01K 11/18; G01K 13/00
[52] U.S. Cl. ................................... 250/339; 250/341; 356/43; 374/161
[58] Field of Search .................. 374/161, 162; 356/43, 356/44, 45, 432, 445; 250/339, 341

[56] References Cited

U.S. PATENT DOCUMENTS

| | | | |
|---|---|---|---|
| 3,462,224 | 8/1969 | Woods et al. | 356/47 |
| 3,635,085 | 1/1972 | Shimotsuma et al. | 73/340 |
| 3,734,620 | 5/1973 | Cade | 356/73 |
| 4,057,349 | 11/1977 | Barrett | 356/45 |
| 4,136,566 | 1/1979 | Christensen | 356/44 X |
| 4,354,105 | 10/1982 | Spirig | 250/231 R |
| 4,355,910 | 10/1982 | Quick et al. | 356/44 X |
| 4,479,848 | 10/1984 | Otsubo et al. | 356/445 X |
| 4,671,651 | 6/1987 | Toyoda et al. | 356/44 |

FOREIGN PATENT DOCUMENTS 57-179648 11/1982 Japan .................................. 356/445

OTHER PUBLICATIONS

Germanova et al., "An Optical Method For Measuring Temperature & Electric Field in Semiconductors", J. Phys. D: Appl. Phys., vol. 11, #17, 1978, pp. 2383-2390.

Primary Examiner—Vincent P. McGraw
Attorney, Agent, or Firm—William G. Auton; Donald J. Singer

[57] ABSTRACT

Semiconductors may be optically tested for their temperatures by illuminating them with tunable monochromatic electromagnetic radiation and observing the light reflected off of them. A transition point will occur when the wavelength of the light corresponds with the actual band gap energy of the semiconductor. At the transition point, the image of the semiconductor will appreciably darken as the light is transmitted through it, rather than being reflected off of it. The wavelength of the light at the transition point corresponds to the actual band gap energy and the actual temperature of the semiconductor.

2 Claims, 1 Drawing Sheet

REFLECTION TECHNIQUE FOR THERMAL MAPPING OF SEMICONDUCTORS

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to the testing of semiconductors, and more specifically to a system which determines the band gap energy of semiconductors from the photoelectric effect of infrared radiation on them, and therefrom determines the temperature of the semiconductor.

The measurement of internal temperature and temperature distribution of semiconductor devices is essential for reliability characterization of these devices and product evaluation and life test stress condition evaluation and power dissipation design analysis. While the performance of semiconductors can be electrically measured directly, and while temperatures can also be measured directly, both the electrical and thermal characteristics of semiconductors can be determined optically by the photoelectric effect of illumination on the semiconductor.

Planck observed that radiation from a heated sample is emitted in discrete units of energy, called quanta; the energy units were described by hv, where v is the frequency of the radiation, and h is a quantity now called Planck's constant ($h = 6.63 \times 10^{-34}$ J-sec). Soon after Planck developed this hypothesis, the discrete nature or quantization of light was discovered in a phenomenon called "the photoelectric effect". When monochromatic light is incident on the surface of a metal plate in a vacuum, the electrons in the metal absorb energy from the light, and some of the electrons receive enough energy to be ejected from the metal surface into the vacuum. If the energy of the escaping electrons is measured, a plot can be made of the maximum energy as a function of the frequency v of the incident light.

The maximum energy $E_m$ is related to the frequency v by the relationship $E_m = hv - q\Phi$ where: q is the magnitude of the electronic charge, and the quantity $\Phi$ (volts) is a characteristic of the particular metal used. When $\Phi$ is multiplied by the electronic charge, an energy (joules) is obtained which represents the minimum energy required for an electron to escape from the metal into a vacuum.

One of the distinguishing characteristics of a semiconductor device is its energy band gap $E_G$. This is the measure of separation between its conductance band and its valence band. The task of determining the energy band gap of semiconductors, using the photoelectric effect, and performing thermal mapping therefrom is alleviated, to some extent, by the systems of the following U.S. Patents, the disclosures of which are incorporated herein by reference:

U.S. Pat. No. 4,380,864 issued to P. K. Das;
U.S. Pat. No. 3,803,413 issued to R. Vanzetti et al;
U.S. Pat. No. 2,790,952 issued to W. J. Pietenpol;
U.S. Pat. No. 3,635,085 issued to T. Shimotsuma et al;
U.S. Pat. No. 3,462,224 issued to W. Woods et al; and
U.S. Pat. No. 4,354,105 issued to E. Spirig.

The Das reference entails the use of electrical measurements of semiconductors when they are under the influence of laser illumination. While electrical measurements do provide an indication of semiconductor performance, a more direct approach would be optial measurements of energy released due to the photoelectric effect.

The Pietenpol and Vanzetti et al references both optically test semiconductors. However, the purpose of the Pietenpol system is to locate semiconductor junctions. The system of Vanzetti et al measures infrared energy radiated from electronic components and compares it with expected results. The disclosure of Shimotsuma et al, Spirig and Woods et al are instructive, and disclose state-of-the-art temperature measurement systems.

From the foregoing discussion, it is apparent that there remains a need to determine the electrical characteristics of semiconductors from the photoelectric effect of infrared radiation, and therefrom perform thermal mapping. The present invention is intended to satisfy that need.

SUMMARY OF THE INVENTION

The present invention is a system which optically determines the band gap energy of semiconductors, and which performs thermal mapping of the semiconductors from the band gap energy.

The thermal mapping of semiconductors in one embodiment of the invention, is accomplished using: a light source, monochrometer, a microscope, a detector, and a cathode ray tube (CRT) display device. The light source and monochrometer act in concert as a source of infrared radiation. The light source can be an incandescent light which emits high intensity light in a biased spectrum. The monochrometer receives and processes the light to produce monochromatic infrared radiation which is reflected off the semiconductor into the microscope, and sent to the detector. The detector may be a charge coupled device (CCD) array or vidicon which detects the semiconductor image from the light from the microscope, and the CRT receives and displays the signals produced by the detector.

In operation, the monochrometer is tuned so that the illumination observed in the microscope changes from illumination that is simply reflected from the semiconductor, the illumination that is transmitted through the semiconductor. The wavelength at which this occurs is the reflection edge wavelength, and the corresponding photon energy is equal to the band gap energy of the semiconductor device. The detector detects the light from the microscope and sends detection signals to the CRT which displays the image in real time. The actual band gap energy indicated in the display is compared with the expected value of band gap energy which occurs at room temperature (300° K.). The differences between the actual band gap energy and the expected band gap energy values corresponds linearly with the change in temperature, so that the actual temperatures of the semiconductor device can be determined.

The band gap energy of the semiconductor is determined by observing the semiconductor image in the display while tuning the monochrometer. As mentioned above, the band gap energy corresponds to the wavelength of light at the transition: where the illumination is transmitted through the semiconductor rather than reflected from the semiconductor. At this transition point, the image on the CRT display will become considerably darkened as an appreciable amount of photon energy ceases to be reflected by the semiconductor. In other words, the semiconductor image will visibly darken at the transition point. The actual wavelength and band gap energy are determined by checking the wavelength setting of the tunable monochrometer at the transition point. Once the actual band gap of the semiconductor is known, the actual temperature of the semiconductor is determined by mathematically comparing the actual band gap energy with the reference band gap energy that occurs at the reference temperature (300° K.).

It is one object of the present invention to perform thermal mapping of semiconductors by photodetection.

It is another object of the present invention to optically determine the band gap energies of semiconductors, and therefrom determine their temperatures.

These objects together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENT

The present is a system which optically determines the band gap energy of semiconductors, and therefrom determines the semiconductor's temperature.

Figure 1:
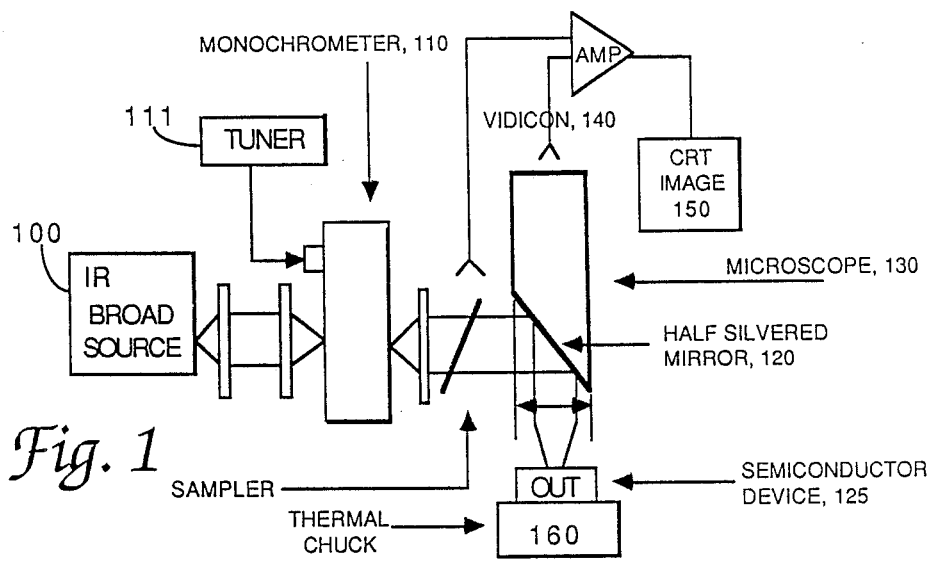
FIG. 1 is a schematic of an embodiment of the present invention.

The reader's attention is now directed towards FIG. 1, which is a schematic of an embodiment of the present invention. The system of FIG. 1 uses a broad spectrum infrared illumination source, 100 and a tunable monochrometer 110 as the source of infrared radiation.

Infrared radiation is electromagnetic radiation having wavelengths between about 0.75 micron and 1000 microns, that is, between those of microwaves and visible red light. This range is sometimes divided into near infared (0.75-3.0 microns), middle infrared (3.0-30.0 microns), and far infrared (30-1000 microns). For the purposes of the present invention, the source 100 and monochrometer 110 should be tunable particularly in the near infrared range. The reason for this is that the semiconductor band gap energies of interest are principally manifested at wavelengths of about one micron.

The infrared radiation is directed by optical mirrors 120 onto the semiconductor device 125 which reflects the light back into a microscope 130. The semiconductor image is relayed by the microscope into an infrared detector 140. The detector may be a charge coupled device (CCD) or vidicon which detects the light from the microscope 130. The CRT 150 displays the signals produced by the detector 140.

The process of the present invention entails adjusting the wavelengths of light emitted by the tunable monochrometer 110 while observing the semiconductor image on the CRT 150. The band gap energy of the semiconductor correponds to the wavelength of light at the transition (the point at which the illumination is transmitted through the semiconductor rather than reflected from the semiconductor). At this transition point, the image on the CRT 150 will become considerably darkened as an appreciable amount of photon energy ceases to be reflected by the semiconductor, but is rather transmitted through the device. Therefore, the monochrometer is tuned until the CRT image darkens, and at that point the CRT tuner 111 is observed to determine the exact wavelength of light being emitted by the monochrometer. This wavelength yields the semiconductor actual band gap energy and therefrom the semiconductor temperature, as discussed below.

As mentioned above, the energy (band) gap is defined as the energy difference between the lower edge of the conduction band and the upper edge of the valence band. The value $E_G/kT$ is indicative of thermal agitation of electrons across the energy gap since the intrinsic carrier concentration depends exponentially upon $E_G/kT$, where $E_G$ equals the energy band gap, and T equals the temperature in degrees K.

Within a limited temperature range the temperature dependence of the energy gap of most semiconductors can be represented by:
$$E_G(T) = E_{Go} - \alpha_G kT$$

$$E_G(T) = E_{Go} - (dE_G/dT)(T - 300° K.) \tag{1}$$

where $E_{Go}$ is the energy gap at the reference temperature (300° K.), k equals the Boltzman constant, and $\alpha_G$ is an empirical constant characteristic of the semiconductor:

$$\alpha_G = (dE_G/dT)(T - 300° K.)/kT \tag{2}$$

From equation 1 above, the actual temperature T of the semiconductor is given by:

$$T = \frac{(E_{GO} - E_{GT})}{\alpha_G k} \text{ where:}$$

$E_{Go}$ equals the reference energy gap of the semiconductor at 300° K.; and $E_{GT}$ equals the actual energy gap observed.

Typical reference energy gaps for known semiconductors are given below in Table 1. Note that all values are at 300° K.

TABLE 1

|      | $E_{Go}$ (eV) |
|------|---------------|
| Si   | 1.11          |
| Ge   | 0.67          |
| SiC($\alpha$) | 2.86  |
| AlP  | 2.45          |
| AlAs | 2.16          |
| AlSb | 1.6           |
| GaP  | 2.26          |
| GaAs | 1.43          |
| GaSb | 0.7           |
| InP  | 1.28          |
| InAs | 0.36          |
| InSb | 0.18          |
| ZnS  | 3.6           |
| ZnSe | 2.7           |
| ZnTe | 2.25          |
| CdS  | 2.42          |
| CdSe | 1.73          |
| CdTe | 1.58          |
| PbS  | 0.37          |
| PbSe | 0.27          |
| PbTe | 0.29          |

Figure 2:
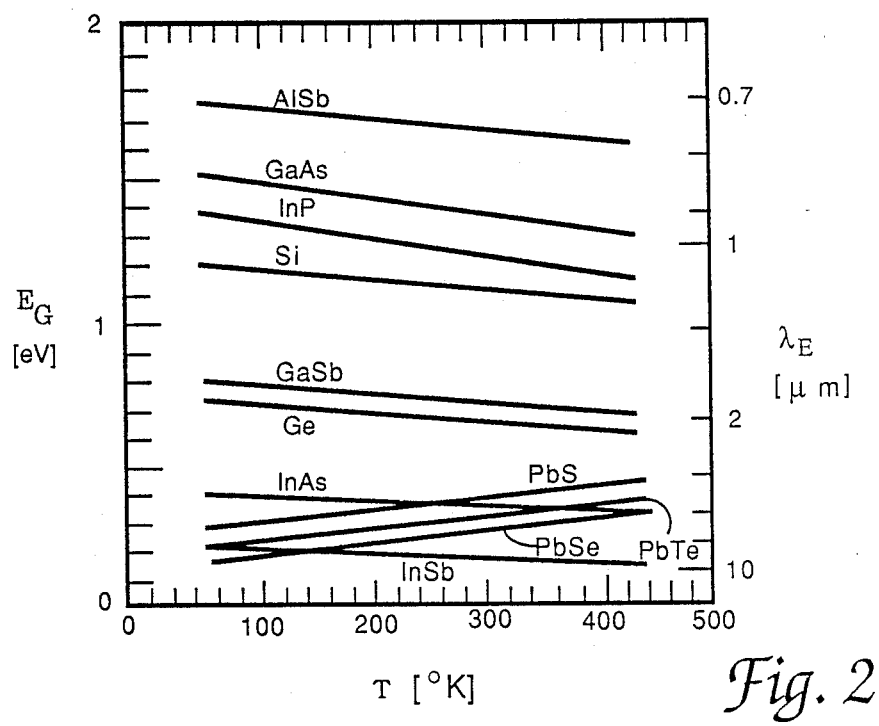
FIG. 2 is a chart which correlates wavelengths of the absorption edge with both the actual energy gap and the actual temperature of several semiconductors.

The reader's attention is now directed towards FIG. 2, which is a chart which correlates the wavelength of the absorption edge ($\lambda_E$) with both the actual energy gap manifested ($E_G$), and the actual semiconductor temperature (° K.). It is assumed that $\lambda_E[\mu m] = 1.237/E_G[eV]$.

Table 2 is a listing of the temperature variation of energy gap in typical semiconductors.

TABLE 2

| Semiconductor | $dE_G/dT(10^{-4} eV/°K.)$ |
|---|---|
| Si | −2.3 |
| Ge | −3.7 |
| AlSb | −4.1 |
| GaAs | −4.3 |
| GaP | −5.4 |
| GaSb | −4.3 |
| InAs | −3.5 |
| InP | −4.5 |
| InSb | −2.9 |

In the temperature range between 100° and 400° K., the energy gap varies nearly linearly with temperature. The empirically determined temperature dependence of $E_G$ of selected semiconductors around 300° K. is given in Table 2. Some lead-containing semiconductors have a positive temperature coefficient of $E_G$, e.g., PbS, PbSe, PbTe.

The invention, as depicted in FIG. 1, may be constructed of equipment which is commercially available. However, the following design considerations should be followed in the selection of equipment. First, as mentioned above, both the IR source 100 and tunable monochrometer 110 should be selected to operate in the near infrared range (0.75-3.0 microns). The reason for this is that several semiconductors of interest have energy band gaps that are manifested at wavelengths of about 1 micron.

The spectral limitations of the optical microscope 130 will limit the temperatures and semiconductor materials which may be observed in this manner. Quartz optics used in good microscopes should allow materials such as GaAs, Si, GaAlAs, AlAs, GaP, and others to be observed in this way.

In addition, when the device is active, some areas of the device will have different temperatures. This should be observable as areas which are reflective and areas which are transparent. The temperatures of these areas can be observed by tuning the monochrometer to observe the reflection edge at these locations. Constant temperature profiles can be seen as the demarcation line between reflecting and transmitting areas.

The spatial resolution of this technique should be the spatial resolution of the microscope at the specific wavelength being used, which will be near the visible region and hence approach 1.0 micrometer. The temperature resolution will be limited by the minimum detectable intensity of light of the detector and the corresponding spectral width of the monochromatic source.

As discussed above, the invention may be described as a process of determining the temperature of a semiconductor. This process may be divided up into the following steps:

illuminating the semiconductor with electromagnetic radiation while incrementally adjusting the electromagnetic radiation's wavelength;

observing the electromagnetic radiation as it reflects off the semiconductor;

detecting a transition point which occurs when said semiconductor reflects a reduced amount of said electromagnetic radiation and transmits some of the electromagnetic radiation;

noting a transition wavelength of the electromagnetic radiation which occurs at the transition point;

ascertaining an actual band gap energy for the semiconductor from the transition wavelength; and determining the actual temperature of the semiconductor from the actual band gap energy and the transition wavelength;

The actual temperature may be either calculated mathematically or determined from a chart, such as illustrated in FIG. 2.

Figure 3:
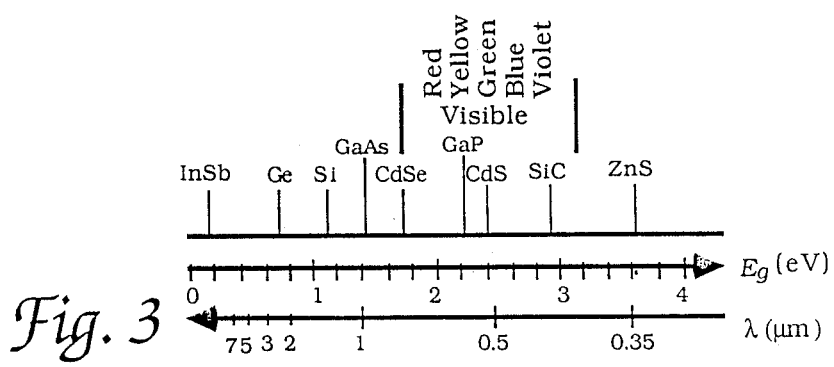
FIG. 3 is a chart which indicates the band gap energies of several semiconductors relative to the visible, infrared, and ultraviolet portions of the spectrum.

FIG. 3 indicates the band gap energies of some of the common semiconductors, relative to the visible, infrared, and ultraviolet portions of the spectrum. Note that GaAs, Si, Ge, and InSb lie outside the visible region, in the infrared. Other semiconductors, such as GaP and CdS, have band gaps wide enough to pass photons with energies equal to the band gap, or larger. Thus, Si absorbs not only band gap light ($\sim 1$ $\mu m$) but also shorter wavelengths, including those in the visible part of the spectrum. Therefore, the present invention can also be implemented by tuning the monchrometer to either visible or non-visible regions of the spectrum, if a detector sensitive to these regions is used. Such detectors need only be capable of providing an indication of a decrease of illumination from the semiconductor to indicate the transition point. As discussed above, the presence of the transition point yields the wavelengths and energy band gaps of the semiconductor. From the actual band gap, the actual semiconductor temperature is determined. Note that such detectors are known in the art and need not be discussed in detail here.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A process of determining a temperature of a semiconductor comprising the steps of:

illuminating the semiconductor with electromagnetic radiation while incrementally adjusting the electromagnetic radiation's wavelength, wherein said illuminating step comprises shining infrared radiation on the semiconductor using a monochrometer while incrementally adjusting wavelengths emitted by the monochrometer, wherein said infrared radiation used in said illuminating step is confined to a near infrared region with wavelengths between 0.75 and 3.0 microns;

producing a semiconductor image by capturing the electromagnetic radiation as it reflects off of the semiconductor by focusing an optical microscope upon the semiconductor to produce thereby said semiconductor image;

detecting a transition point which occurs when said semiconductor reflects a reduced amount of said electromagnetic radiation and transmits some of the electromagnetic radiation, wherein said detecting step comprises using an infrared-sensitive detector to sense the semiconductor image from the microscope while receiving an indication of a decrease of illumination in the semiconductor image as the monochrometer is incrementally tuned, the decrease of illumination being an indication of the transition point;

noting a transition wavelength of the electromagnetic radiation which occurs at the transition point, wherein the transition wavelength corresponds with a setting of wavelength of the electromagnetic radiation emitted by the monochrometer at the transition point;

ascertaining an actual band gap energy for the semiconductor from the transition wavelength; and determining the actual temperature of the semiconductor from the actual band gap energy and transition wavelength, wherein the determining step comprises performing a mathematical calculation using the equation:

$$T = \frac{E_{GO} - E_{GT}}{\alpha_G k} \text{ where;}$$

T equals the temperature of the semiconductor;

$E_{GT}$ equals the actual band gap energy of the semiconductor;

$E_{Go}$ equals a reference band gap energy for the semiconductor which occurs at a reference temperature of 300° K.;

$\alpha_G$ equals an empirical constant characteristics of the semiconductor; and k equals a Boltzmann constant.

2. A device for determining a semiconductor's actual temperature comprising:

an infrared source which emits a broad spectrum of light;

a tunable monochrometer which receives said broad spectrum of light from said infrared source and produces therefrom an illuminating monochromatic radiation at tunable wavelengths, said illuminating monochromatic radiation being reflected off of said semiconductor, said tunable monochrometer also indicating to users a value of the illuminating monochromatic radiation's wavelength actually being emitted;

a microscope which receives light reflected off of said semiconductor from said illuminating source to produce an image of said semiconductor;

a detector which receives and converts said image of said semiconductor from said microscope and converts said image into electrical signals; and a display means which receives said electrical signals from said detector and displays said semiconductor image as said tunable monochrometer is incrementally tuned, said display means indicating a decrease of light reflected off of said semiconductor at a transition point where said illuminating monochromatic radiation is transmitted through the semiconductor rather than reflected off of it, said transition point occuring at a specific wavelength which corresponds to the semiconductor's actual band gap energy and actual temperature, said specific wavelength being the value of the monochromatic radiation's wavelength actually emitted by the tunable monochrometer at the transition point.

* * * * *